(12) United States Patent
Holmberg

(10) Patent No.: US 7,815,933 B2
(45) Date of Patent: *Oct. 19, 2010

(54) SELF EMULSIFYING DRUG DELIVERY SYSTEM

(75) Inventor: Christina Holmberg, Södertälje (SE)

(73) Assignee: Nicox S.A., Sophia Antipolis (FR)

( * ) Notice: Subject to any disclaimer, the term of this patent is extended or adjusted under 35 U.S.C. 154(b) by 821 days.

This patent is subject to a terminal disclaimer.

(21) Appl. No.: 10/488,585

(22) PCT Filed: Sep. 5, 2002

(86) PCT No.: PCT/SE02/01598

§ 371 (c)(1),
(2), (4) Date: Mar. 4, 2004

(87) PCT Pub. No.: WO03/022249

PCT Pub. Date: Mar. 20, 2003

(65) Prior Publication Data

US 2004/0248974 A1    Dec. 9, 2004

(30) Foreign Application Priority Data

Sep. 7, 2001   (SE)   ................... 01029933

(51) Int. Cl.
A61K 9/127   (2006.01)
A61K 9/10    (2006.01)
A61K 9/107   (2006.01)

(52) U.S. Cl. .................. 424/450; 514/78; 514/937; 514/938

(58) Field of Classification Search ................. 424/450; 514/78, 937, 938
See application file for complete search history.

(56) References Cited

U.S. PATENT DOCUMENTS

| | | | |
|---|---|---|---|
| 4,255,431 A | 3/1981 | Junggren et al. | |
| 4,369,182 A * | 1/1983 | Ghyczy et al. | 514/569 |
| 4,508,905 A | 4/1985 | Junggren et al. | |
| 4,554,276 A | 11/1985 | LaMattina | |
| 4,562,261 A | 12/1985 | Hirata et al. | |
| 4,619,934 A | 10/1986 | Sunshine et al. | |
| 4,676,984 A | 6/1987 | Wu et al. | |
| 4,704,278 A | 11/1987 | Wu et al. | |
| 4,757,060 A | 7/1988 | Lukacsko et al. | |
| 4,758,579 A | 7/1988 | Kohl et al. | |
| 4,766,117 A | 8/1988 | Crawford et al. | |
| 4,786,505 A | 11/1988 | Lovgren et al. | |
| 4,965,065 A | 10/1990 | Lukacsko et al. | |
| 5,037,815 A | 8/1991 | Lukacsko et al. | |
| 5,043,358 A | 8/1991 | Lukacsko et al. | |
| 5,204,118 A | 4/1993 | Goldman et al. | |
| 5,260,333 A | 11/1993 | Lukacsko et al. | |
| 5,364,616 A | 11/1994 | Singer et al. | |
| 5,373,022 A | 12/1994 | Fawzi et al. | |
| 5,417,980 A | 5/1995 | Goldman et al. | |
| 5,466,436 A | 11/1995 | Stables | |
| 5,514,663 A | 5/1996 | Mandel | |
| 5,631,022 A | 5/1997 | Mandel et al. | |
| 5,643,960 A | 7/1997 | Breitner et al. | |
| 5,686,105 A | 11/1997 | Kelm et al. | |
| 5,716,648 A | 2/1998 | Halskov et al. | |
| 5,929,030 A | 7/1999 | Hamied et al. | |
| 5,932,243 A | 8/1999 | Fricker et al. | |
| 5,955,451 A * | 9/1999 | Lichtenberger et al. | 514/78 |
| 5,965,160 A * | 10/1999 | Benita et al. | 424/455 |
| 6,013,281 A | 1/2000 | Lundberg et al. | |
| 6,025,395 A | 2/2000 | Breitner et al. | |
| 6,054,136 A | 4/2000 | Farah et al. | |
| 6,160,020 A | 12/2000 | Ohannesian et al. | |
| 6,162,816 A | 12/2000 | Bohlin et al. | |
| 6,207,188 B1 | 3/2001 | Gustavsson et al. | |
| 6,231,888 B1 | 5/2001 | Lerner et al. | |
| 6,267,985 B1 | 7/2001 | Chen et al. | |

(Continued)

FOREIGN PATENT DOCUMENTS

| | | |
|---|---|---|
| DE | 4 131 678 A1 | 10/1992 |
| DE | 198 01 811 A1 | 1/1998 |
| EP | 0005129 | 4/1981 |
| EP | 0 166 287 A1 | 1/1986 |
| EP | 0274870 A2 | 7/1988 |
| EP | 0274870 A3 | 7/1988 |
| EP | 0174726 | 4/1989 |
| EP | 0 320 550 A1 | 6/1989 |
| EP | 0116287 | 8/1989 |
| EP | 0 426 479 A1 | 5/1991 |

(Continued)

OTHER PUBLICATIONS

Amidon et al., Pharmaceut. Res., 12(1995), pp. 413-420.
N.H. Shah et al., Intl. J. Pharmaceut., 106 (1994), pp. 15-23.
W.J. Bowtle, Pharmaceutical Tech. Europe, Oct. 1998, 84-90.
E.T. Coole, Pharmaceut. Tech. Intl., Sept./Oct. 1989, 29-33.
J.S. Burns et al., Intl. J. Pharmaceut., 141 (1996), pp. 9-16.

(Continued)

*Primary Examiner*—Gollamudi S Kishore
(74) *Attorney, Agent, or Firm*—Arent Fox LLP

(57) ABSTRACT

The present invention claims and discloses a pharmaceutical composition suitable for oral administration, in form of an emulsion pre-concentrate, comprising (i) one or more NO-releasing NSAID(s); (ii) one or more surfactants, of which at least one is phospholipid; said composition forming an in-situ oil-in-water emulsion upon contact with gastrointestinal fluids. The composition may optionally also comprise an additional oil or semi-solid fat. Further, one or more short-chain alcohols can optionally be included in the composition. Also within the scope of the invention is a combination with a proton pump inhibitor. The pharmaceutical composition is useful in the treatment of pain and inflammation. Further within the scope of the invention is kit comprising a pharmaceutical composition according to the invention in a unit dosage form, in combination with a proton pump inhibitor, and said proton pump inhibitor is enteric coated.

13 Claims, No Drawings

U.S. PATENT DOCUMENTS

| | | | |
|---|---|---|---|
| 6,312,704 | B1 | 11/2001 | Farah et al. |
| 6,365,184 | B1 | 4/2002 | Depui et al. |
| 6,395,298 | B1 | 5/2002 | Flanagan et al. |
| 6,436,430 | B1 | 8/2002 | Mulye |
| 6,485,747 | B1 | 11/2002 | Flanagan et al. |
| 6,544,556 | B1 | 4/2003 | Chen et al. |
| 6,613,354 | B2 | 9/2003 | Depui et al. |
| 6,635,281 | B2 | 10/2003 | Wong et al. |
| 2001/0025107 | A1 | 9/2001 | Barberich et al. |
| 2001/0036473 | A1 | 11/2001 | Scott et al. |
| 2001/0044410 | A1 | 11/2001 | Gelber et al. |
| 2002/0012676 | A1 | 1/2002 | Lundberg et al. |
| 2002/0042433 | A1 | 4/2002 | Yelle et al. |
| 2002/0044962 | A1 | 4/2002 | Cherukuri et al. |
| 2002/0045184 | A1 | 4/2002 | Chen |
| 2002/0086029 | A1 | 7/2002 | Lundberg et al. |
| 2002/0111370 | A1 | 8/2002 | Bergman et al. |
| 2002/0155153 | A1 | 10/2002 | Depui et al. |
| 2003/0008903 | A1 | 1/2003 | Barberich et al. |
| 2003/0113375 | A1 | 6/2003 | Lundberg et al. |
| 2003/0129235 | A1 | 7/2003 | Chen et al. |
| 2004/0052824 | A1 | 3/2004 | Chacra-Vernet et al. |

FOREIGN PATENT DOCUMENTS

| | | | |
|---|---|---|---|
| EP | 0 426 479 | B1 | 5/1991 |
| EP | 0 550 083 | B1 | 7/1993 |
| EP | 0984012 | A3 | 1/2001 |
| GB | 2 105 193 | A | 3/1983 |
| GB | 2163747 | A | 3/1986 |
| WO | 85/03443 | A1 | 8/1985 |
| WO | 90/06925 | A1 | 6/1990 |
| WO | WO-95/06925 | | 6/1990 |
| WO | 93/12817 | A1 | 7/1993 |
| WO | WO-94/04484 | | 3/1994 |
| WO | 94/07541 | A1 | 4/1994 |
| WO | WO-94/12463 | | 6/1994 |
| WO | WO-94/27988 | | 12/1994 |
| WO | WO-95/01977 | A1 | 1/1995 |
| WO | WO-95/08983 | | 4/1995 |
| WO | WO-95/09831 | | 4/1995 |
| WO | WO-95/30641 | | 11/1995 |
| WO | WO-96/01623 | | 1/1996 |
| WO | 97/25064 | * | 7/1997 |
| WO | 98/22117 | A1 | 5/1998 |
| WO | 99/00380 | A1 | 1/1999 |
| WO | 99/12524 | A1 | 3/1999 |
| WO | 99/56727 | A2 | 11/1999 |
| WO | WO-00/57885 | | 10/2000 |
| WO | 00/71122 | A1 | 11/2000 |
| WO | 00/72838 | A1 | 12/2000 |
| WO | WO-00/72838 | A1 | 12/2000 |
| WO | WO-01/66088 | A1 | 9/2001 |
| WO | 03/017980 | A1 | 3/2003 |

OTHER PUBLICATIONS

Bigard et al., "Complete Prevention by Omeprazole of Aspirin Induced Gastric Lesions in Healthy Subjects," GUT 29A712, T49, 1988.
Bombardier et al., "Comparison of Upper Gastrointestinal Toxicity of Rofecoxib and Naproxen in Patients with Rheumatoid Arthritis," N. Engl. J. Med. 343 1520-1528, 2000.
Brown et al., "Prevention of the Gastrointestinal Adverse Effects of Nonsteroidal Anti-Inflammatory Drugs," Prac. Drug Safety 21 503-512, 1999.
Cullen et al., "Primary Gastroduodenal Prophylaxis with Omeprazole for Non-Steroidal Anti-Inflammatory Drug Users," Aliment. Pharmacol. Ther. 12 135-140, 1998.
Dent, "Why Proton Pump Inhibition Should Heal and Protect Against Nonsteroidal Anti-Inflammatory Drug Ulcers," Am. J. Med. 104 52S-55S, 1998.
Hawkey, "Progress in Prophylaxis Against Nonsteroidal Anti-Inflammatory Drug-Associated Ulcers and Erosions," Am. J. Med. 104 67S-74S, 1998.
Hawkey et al., "Omeprazole Compared with Misoprostol for Ulcers Associated with Nonsteroidal Anti-inflammatory Drugs," N. Engl. J. Med. 338 727-734, 1998.
Howden, "Clinical Pharmacology of Omeprazole," Clin. Pharmacokinet. 20 38-49, 1991.
Katz et al., "Gastric Acidity and Acid Breakthrough with Twice-Daily Omeprazole or lansoprazole," Aliment. Pharmacol. Ther 14 709-714, 2000.
Kephart et al., "Coprescribing of nonsteroidal Anti-Inflammatory Drugs and Cytoprotective and Antiulcer Drugs in Nova Scotia's Senior Population," Clin. Ther. 17 1159-1173, 1995.
Kimmey et al., "Role of H2-Receptor Blockers in the Prevention of Gastric Injury Resulting from Nonsteroidal Anti-inflammatory Agents," Am. J. Med. 84 49-52, 1988.
Lad et al., "Management of Nonsteroidal Anti-Inflammatory Drug-Induced Gastroduodenal Disease by Acid Suppression," Can. J. Gastroenterol 13 135-142, 1999.
Lee et al., "Omeprazole Prevents Indomethacin-Induced Gastric Ulcers in Rabbits," Aliment. Pharmacol. Ther. 10, 571-576, 1996.
Lichtenberger et al., "Nonsteroidal Anti-Inflammatory Drug and Phospholipid Prodrugs: Combination Therapy with Antisecretory Agents in Rats," Gastroenterology 111, 990-995, 1996.
Mattsson et al., "Omeprazole Provides Protection Against Experimentally Induced Gastric Mucosal Lesions," Eur J. Pharmacol. 91, 111-114, 1983.
Oddsson et al., "Endoscopic Findings in the Stomach and Duodenum after Treatment with Enteric-Coated and Plain Naproxen Tablets in Healthy Subjects," Scand. J. Gastroenterol. 25, 231-234, 1990.
Savarino et al., "Effect of One-Month Treatment with Nonsteroidal Antiinflamatory Drugs (NSAIDs) on Gastric pH of Rheumatoid Arthritis Patients," Digestive Disease and Sciences 43, 459-463, 1998.
Scheiman, "NSAID-Induced Peptic Ulcer Disease: A Critical Review of Pathogenesis and Management," Dig. Dis. 12, 210-222, 1994.
Selway, "Potential Hazards of Long-Term Acid Suppression," Scand J. Gastroenterol. 25 (Supp. 178), 85-92, 1990.
Silverstein et al.,"Gastrointestinal Toxicity with Celecoxib vs. Nonsteroidal Anti-Inflammatory Drugs for Osteoarthritis and Rheumatoid Arthritis; The CLASS Study: A Randomized Controlled Trial," JAMA 284, 1247-1255, 2000.
Trondstad et al., "Gastroscopic Findings after Treatment with Enteric-Coated and Plain Naproxen Tablets in Healthy Subjects," Scand. J. Gastroenterol. 20, 239-242,1985.
Wagner et al., "Effects of Nonsteroidal Antiinflammatory Drugs on Ulcerogenesis and Gastric Secretion in Pylorus-Ligated Rat," Digestive Diseases and Sciences 40, 134-140, 1995.
Wolfe et al., "Gastrointestinal Toxicity of Nonsteroidal Anti-Inflammatory Drugs," N. Engl. J. Med. 340, 1888-1899, 1999.
Yeomans et al., "A Comparison of Omeprazole with Ranitidine for Ulcers Associated with Nonsteroidal Anti-Inflammatory Drugs," N. Engl. J. Med. 338, 719-726, 1998.
Yeomans, "New Data on Healing of Nonsteroidal Anti-Inflammatory Drug-Associated Ulcers and Erosions," Am. J. Med. 104, 56S-61S, 1998.
Young, "Liquid Fill of Two Piece Hard Shells—A Fluid Solution to Current Problems", Pharm. Mfg. Packing Sourcer, Mar. 1999, pp. 14-22.

* cited by examiner

SELF EMULSIFYING DRUG DELIVERY SYSTEM

CROSS-REFERENCE TO RELATED APPLICATION

This application is a National Stage entry of International Application No. PCT/SE02/01598, having international filing date of Sep. 5, 2002, which claims priority to SE 0102993-3, filed Sep. 7, 2001, the disclosure of each of which is hereby incorporated in its entirety by reference.

FIELD OF THE INVENTION

The present invention is directed to a new pharmaceutical composition in form of an emulsion pre-concentrate, a unit dosage form comprising said composition, its use in therapy as well as a process for the preparation thereof.

BACKGROUND AND PRIOR ART

Non-steroidal anti-inflammatory drugs, commonly abbreviated NSAIDs, are well-known drugs for the treatment of pain and inflammation. One of the major drawbacks with NSAIDs is that they have severe gastro-intestinal side effects. Patients undergoing treatment with NSAIDs for a longer period of time, such as naproxen, often experience problems with stomach gastrointestinal side effects.

Nitrogen oxide releasing NSAID compounds (in the following NO-releasing NSAIDs), have recently been found to have an improved side-effect profile, see e.g. WO 94/04484, WO 94/12463, WO 95/09831 and WO 95/30641.

NO-releasing NSAIDs are lipophilic compounds with poor aqueous solubility. They can be classified into class 2 according to the Biopharmaceutical Classification System proposed by Amidon et al. (*Pharm. Res.* 12 (1995) pp. 413-420). Drugs of this class are characterised by low aqueous solubility but reasonably well permeability. A biopharmaceutical problem with these compounds is that their absorption from the gastrointestinal tract (GIT) may be dissolution rate limited, resulting in poor bioavailbility upon oral administration.

WO 95/08983 discloses a self-emulsifying composition for oral administration that forms a microemulsion in situ when in contact with biological fluids. This composition can be characterised as a self-microemulsifying drug delivery system (SMEDDS), and comprises at least an active compound,
lipophilic phase consisting of a mixture of glycerides and fatty acid esters,
a surface-active agent,
a co-surfactant, and
a hydrophilic phase, which is achieved after ingestion by the physiological liquid of the digestive medium.

The present invention distinguishes in several aspects from WO 95/08983 and other SMEDDS.

U.S. Pat. No. 5,929,030 discloses pre-concentrate of a microemulsion as a suitable pharmaceutical composition for a water-insoluble pharmaceutically active substance such as cyclosporin. The composition, that forms a microemulsion, comprises a) a water-insoluble pharmaceutically active material; b) a lipophilic phase comprising a mixture of glycerides, and c) a phospholipid and another surfactant.

Whereas the compositions disclosed in WO 95/08983 and in U.S. Pat. No. 5,929,030 form a microemulsion in situ, the compositions of the present invention form an emulsion. EP 274 870 discloses a pharmaceutical composition comprising a non-steroidal anti-inflammatory drug (NSAID) and a surfactant, the composition being capable of forming micelles containing the NSAID upon oral administration. These micelles have been found to present a particularly appropriate form to administer NSAIDs orally, alleviating their adverse effects on the gastrointestinal tract (GIT). Micelles are aggregates in which the surfactant molecules are generally arranged in a spheroidal structure with the hydrophobic region at the core shielded, in an aqueous solution, from the water by a mantle of outer hydrophilic regions. The drug is usually solubilised in the surfactant. Micelles are to be contrasted in terms of their structure with emulsions, which are formed by compositions of the present invention. Whereas micelles are thermodynamically stable one-phase-systems (according to the Gibbs phase law) in which the aggregates usually have a diameter of approximately two lengths of the surfactant molecule forming it, i.e. in the order of some ten to hundred Angstrom (Å), emulsions are much larger aggregates, in the order of nanometers to micrometers in diameter, consisting of an oily core which is surrounded by one or several layers of surfactants. Emulsions are generally two-phase-systems, and they are thermodynamically unstable (but may be kinetically stable). Another major difference between the compositions of EP 274 870 and the present invention is the nature of the active compound. Whereas NSAIDs are crystalline powders by nature, the NO-releasing NSAIDs or mixtures of NO-releasing NSAIDs used in the present invention are in oil form or in a semisolid form. Moreover, micelles usually require a much higher drug:surfactant ratio compared to the oil:surfactant ratio required to form an emulsion.

One of the unique features with NO-releasing NSAIDs is that many of these compounds are oils or thermosoftening semisolids, which are practically insoluble in water. With high-dose NO-releasing NSAIDs, e.g. when the dose is above about 350 mg, it is difficult to formulate a tablet of reasonable size of the large amount of oil or semisolid. The lipophilic NO-releasing NSAIDs can, however, be formulated as oil-in-water emulsions where the compound constitutes, or is part of, the oil phase emulsified in water by one or more surfactants. An addition of a lipophilic solubiliser phase is not needed for the present invention since the active compound, the NO-releasing NSAID, is able to solely constitute the oil phase of the in situ emulsion. Further, the addition of a co-surfactant can be avoided by the present invention, i.e. the toxicological concern is reduced to a minimum. In pharmacokinetic animal studies it has been surprisingly found that such oil-in-water emulsions of NO-releasing NSAIDs display a much better bioavailability compared to the unemulsified substance. A problem with emulsions is, however, that they are thermodynamically unstable and have poor long-term storage stability since they often tend to coalescence, creaming/sedimentation or phase separation. It is inter alia not possible to fill oil-in-water emulsions into gelatine capsules since the high water content of the emulsion is incompatible with the capsule shell and would dissolve it.

OUTLINE OF THE INVENTION

The problems mentioned above have now been solved by providing a novel Self Emulsifying Drug Delivery System, commonly known as SEDDS, suitable for oral administration. More particularly, the present invention is directed to a pharmaceutical composition suitable for oral administration, in form of an emulsion pre-concentrate, comprising (i) one or more NO-releasing NSAID(s);

(ii) a phospholipid optionally together with one or more other surfactants;

(iii) optionally an oil or semi-solid fat;

said composition forming an in-situ oil-in-water emulsion upon contact with aqueous media such as gastrointestinal fluids.

The composition according to the present invention may optionally further comprise one or more short-chain alcohols.

The composition will form an in situ oil-in-water emulsion of small droplets of nanometer to micron size upon contact with gastrointestinal fluids, the droplets being constituted of one or more NO-releasing NSAIDs forming the core of the droplet, which is covered by one or several layers of surfactant. The in situ formed oil-in-water emulsion will provide a good bioavailability of the NO-releasing NSAID upon oral administration. Storage stability of the emulsion is not a concern since the emulsion is not formed until the pre-concentrate has been taken by the patient, i.e. first at the moment of administration. The possibly unpleasant taste of the pre-concentrate is not a problem when filled into capsules.

The pharmaceutical composition according to the present invention is an emulsion pre-concentrate at the time of administration to a patient. The emulsion pre-concentrate can be filled into unit dosage forms such as capsules, drinking ampoules and dose cushions, or may alternatively be formed as other suitable dosage forms such as chewable soft pills and chewy-base lozenges.

Upon contact with aqueous media such as gastrointestinal fluids, the emulsion pre-concentrate transforms into an oil-in-water emulsion. Thus, the composition will form an in-situ oil-in-water emulsion in the gastrointestinal tract (GI tract). The drug release rate of the composition is determined by the droplet size of the in situ emulsion and the polarity of the emulsion droplets, the latter being governed by the hydrophilic-lipophilic balance (HLB) of the drug/surfactant mixture, and the concentration of the surfactant. Generally, small droplet size and high polarity gives rise to a high drug release rate (N. H. Shah et al., *Int. J. Pharm.* 106 (1994), pp. 15-23).

The wording "NSAID" is defined as a non-steroidal anti-inflammatory drug, i.e. any drug having an anti-inflammatory effect, but which compound does not belong to the compound class "steroids". A person skilled in the art will know whether a compound falls under the definition NSAID. Examples of specific NSAIDs are naproxen, diclofenac, aceclofenac, indomethacine, ketorolac, sulindac, meloxicam, piroxicam, tenoxicam, ibuprofen, ketoprofen, naproxen, azapropazon, nabumetone, carprofen, tiaprofenic acid, suprofen, indoprofen, etodolac, fenoprofen, fenbufen, flurbiprofen, bermoprofen, pirazolac, zaltoprofen, nabumetone, bromfenac, ampiroxicam, and lornoxicam. This list should however not be considered as exhaustive in any way. The wording "NO-releasing NSAID" is contemplated to include any non-steroidal anti-inflammatory drug (NSAID), a salt or an enantiomer thereof, which has the capability to release nitrogen oxide.

NO-releasing NSAIDs are lipophilic compounds with poor aqueous solubility. They can be classified into class 2 according to the Biopharmaceutical Classification System proposed by Amidon et al. (*Pharm. Res.* 12 (1995) 413-420). Drugs of this class are characterised by low aqueous solubility but reasonably well permeability. A biopharmaceutical problem with these compounds is that their absorption from the gastro-intestinal tract (GIT) may be dissolution rate limited resulting in poor bioavailibility upon oral administration.

Preferred NO-releasing NSAIDs in accordance with the present invention, are compounds of the formula I

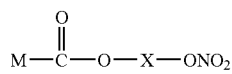

I wherein

X is a spacer, i.e. a compound forming a bridge between the nitrogen oxide donating group and the NSAID; and M is selected from anyone of

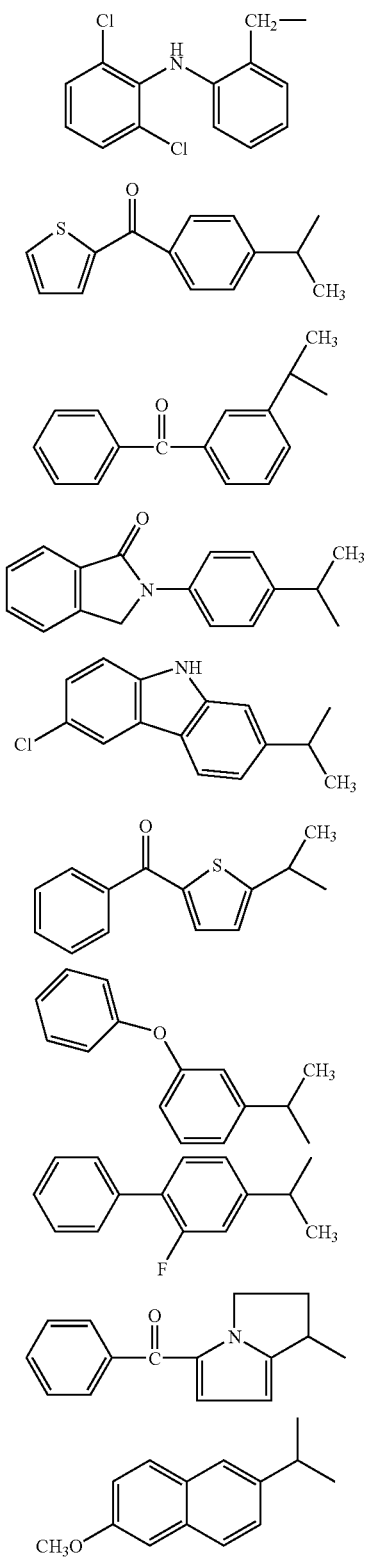

-continued

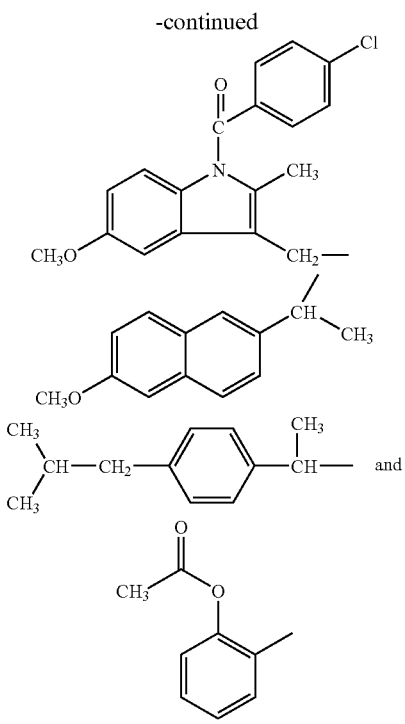

In a preferred embodiment of the invention, the spacer X is selected from a linear, branched or cyclic alkylene group —(CH$_2$)—$_n$ wherein n is an integer of from 2 to 10; and —(CH$_2$)$_m$—O—(CH$_2$)$_p$— wherein m and p are integers of from 2 to 10; and —(CH$_2$)$_p$—C$_6$H$_4$—CH$_2$— wherein p is an integer from 2 to 10.

In one embodiment of the invention, NO-releasing NSAIDs contemplated as active compound(s) in the SEDDS formulation according to the present invention, are compounds disclosed and claimed in WO 94/04484, WO 94/12463, WO 95/09831 and WO 95/30641, which are hereby incorporated by reference.

Specific NO-releasing substances useful in accordance with the present invention are

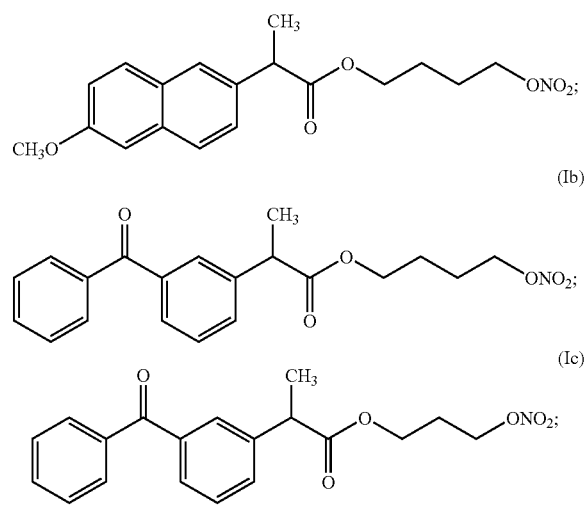

-continued

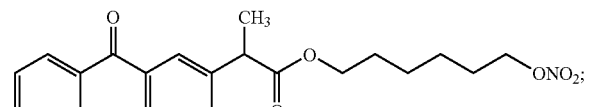
(Id)

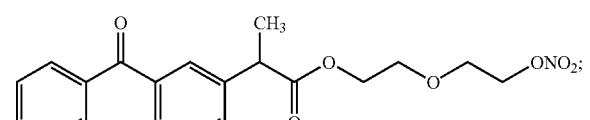
(Ie)

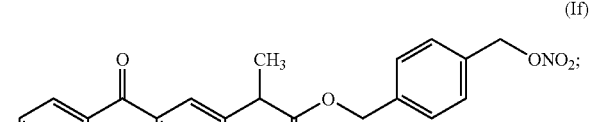
(If)

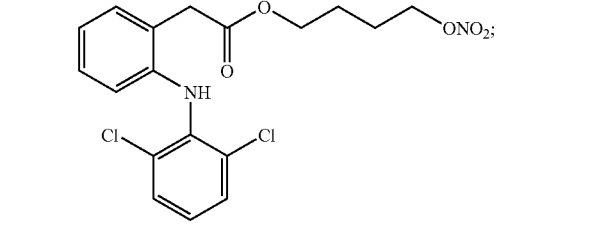
(Ig)

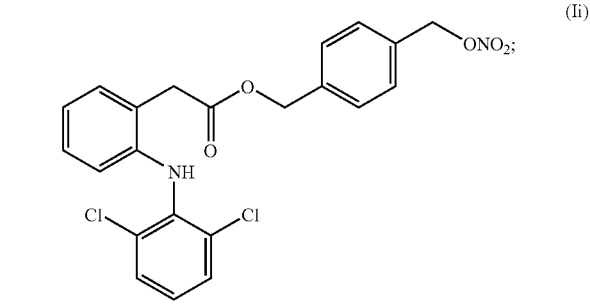
(Ii)

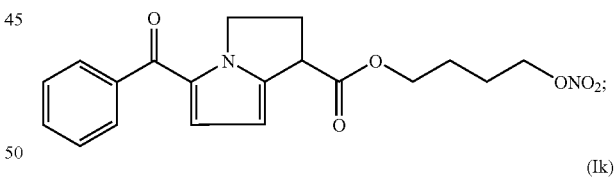
(Ij)

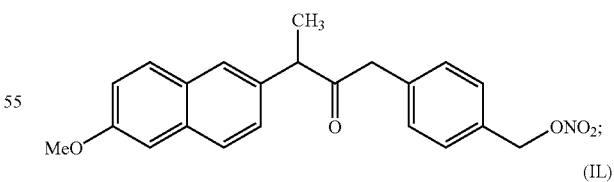
(Ik)

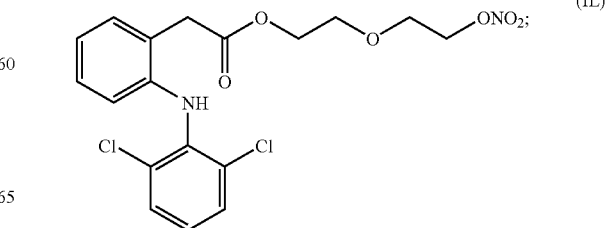
(IL)

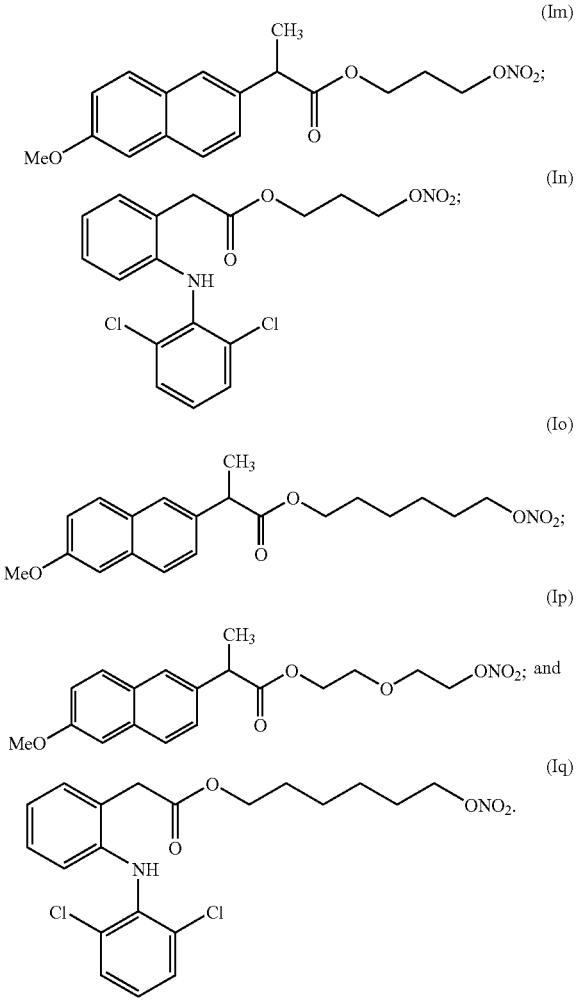

NSAIDs are by nature in form of a powder, whereas NO-releasing NSAIDs predominantly provide a compound in semisolid form or in oil form as such, due to the spacer. This unique feature provides the advantage that no external lipophilic oil or semisolid matrix needs to be added to the emulsion pre-concentrate, since this is an inherent feature of the drug. Additionally, a pharmacologically inert oil or semisolid fat may be added to the pharmaceutical composition by means of a filler or as a viscosity regulator. A filling agent may be required to increase dosing accuracy for low dose compounds. A viscosity regulator may be required in order to adjust optimal viscosity for filling of the composition into e.g. capsules. In particular high speed liquid filling of capsules requires careful adjustment of viscosity within a range that prevents splashing on the low viscosity end and thread-formation on the high viscosity end. Moreover, the viscosity range must be chosen so as to give a pumpable formulation. The viscosity range typically required for liquid filling of capsules is from 0.1 to 25 Pa s.

The total amount of NO-releasing NSAID(s) used in the composition of the invention is preferably in the range 50-1500 mg per unit dose. In still a further preferred embodiment, the amount of NO-releasing NSAID(s) used in the composition is 125-500 mg per unit dose.

The wording "unit dose" is defined as the amount of active compound administered in one single capsule, or dissolved in one glass of water.

The wording "phospholipid" is defined as a non-ionic surfactant comprising a phosphatidyl choline, a diglyceride linked to a choline ester of phosphoric acid. Different fatty acids are bound to the glyceride such as stearic acid, palmitic acid, oleic acid, linoleic acid, linolenic acid. The origin of the phospholipid determines the content of the fatty acids linked. Further, the phosphatidylcholine can be hydrogenated as well, i.e. the fatty acid moieties have been modified. The phospholipids used can be of both natural origin or synthetic. Natural phospholipids are, for example, lecithin. Natural phospholipids are a mixture of various phospholipids and accompanying substances. The content of phosphatidylcholine indicates the product, for example, LIPOID E80, denotes composition with egg lecithin comprising a specified mixture of the chains. Any lecithin can be used but the preferred lecithins are from soya or egg. Suitable lecithins are LIPOID® S40 (soya lecithin) and LIPOID® E80 (egg lecithin). The number defines the content of phosphatidylcholine.

The wording "surfactant" is defined as surface-active amphiphilic compounds such as block co-polymers. Preferred surfactants in accordance with the present invention are non-ionic surfactants, for example those containing polyethylene glycol (PEG) chains, particularly block co-polymers such as poloxamers.

Examples of suitable poloxamers are Poloxamer 407 (Pluronic F127®); Poloxamer 401 (Pluronic L121®); Poloxamer 237 (Pluronic F87®); Poloxamer 338 (Pluronic F138®); Poloxamer 331 (Pluronic L101®); Poloxamer 231 (Pluronic L81®); tetrafunctional polyoxyethylene polyoxypropylene block copolymer of ethylene diamine, known as Poloxamine 908 (Tetronic 908®); Poloxamine 1307 (Tetronic 1307®); Poloxamine 1107 polyoxyethylene polyoxybutylene block copolymer, known as Polyglycol BM45®. This list is only intended to serve as exemplification of surfactants that may be used in accordance with the present invention, and should not in any way be considered as exhaustive or as limiting the invention.

Also a co-surfactant may be added the surfactant above. The co-surfactant has a property as an enhancer of the emulsifying effect of the surfactant. Co-surfactant suitable for the unit dosage form of the invention is, for example, caprylocaproyl macroglycerides.

The total amount of surfactant(s) per unit dosage form in accordance with the invention may be within the range of from 12.5-6000 mg, preferably of from 100-500 mg. The amount phospholipid is 5-20% by weight, of the total amount of surfactants. The ratio NO-releasing NSAID:phospholipid/surfactant may vary from 1:0.1 to 1:10, preferably from 1:0.3 to 1:3.

All phospholipids, surfactants and co-surfactants described above are commercially available from e.g. LIPOID, BASF, Dow Chemicals, and Gattefossé.

In one aspect of the present invention, an oily (lipophilic) or semi-solid NO-releasing NSAID is used as the active ingredient.

If additional oil is added to the pharmaceutical composition this may be any oil as long as it is inert and compatible with the capsule material, as well as being acceptable for use in pharmaceuticals. A person skilled in the art will appreciate which oil to select for the intended purpose. Examples of suitable oils that may be used in accordance with the present invention are vegetable oils such as coconut oil, corn oil, soybean oil, rape seed oil, safflower oil and castor oil. Also animalic oils such as fish oil or one or more mono-, di- and triglycerides are suitable for the purposes of the present invention.

If a semi-solid fat is used as a filler for the pharmaceutical composition, this may preferably be selected from mono-, di- and triglycerides, and fatty acid alcohol such as stearyl alcohol, Gelucires 33/01®, 39/01®, 43/01®, glyceryl palmitostearate such as Precirol ATO5®. Gelucire® is a mixture obtained by mixing mono-, di-, and tri-esters of glycerol, mono- and di-esters of polyethylene glycol, or free polyethylene glycol.

If an additional oil or semi-solid fat is used in the pharmaceutical composition according to the invention, this may serve as a filler or as a viscosity regulator.

The wording "short-chain alcohols" used in accordance with the present invention is herein defined as linear or branched mono-, di- or tri-alcohols having 1-6 carbon atoms. Examples of such short-chain alcohols useful in accordance with the invention are ethanol, propylene glycol and glycerol.

If a short-chain alcohol is added to the pharmaceutical composition according to the invention, the solubility is enhanced and a smaller amount of surfactant is required.

In another aspect of the invention, two or more NO-releasing NSAIDs are used as active ingredients, where anyone of said drugs may be present as an oil or as a semi-solid, or where at least one of said drugs is present as an oil or as a semi-solid and the other one(s) may be present as a solid which is dissolved or suspended in the oily or semi-solid compound. Combinations of two or more NO-releasing NSAIDs may be advantageous in case the high NO-load of a high-dose low potent NO-releasing NSAID is desired to be supplemented with a low dose of high potent NO-releasing NSAID.

A further aspect of the invention is a combination of one or more NO-releasing NSAIDs and an acid susceptible proton pump inhibitor (PPI) compound. The NO-releasing NSAIDs should be formulated such that it is emulsified in the stomach, i.e. as a SEDDS formulation as described above, while the acid susceptible proton pump inhibitor (PPI) must be protected from contact with the acidic gastric juice by for instance an enteric coating. The enteric coating layered PPI remain unaffected until it reaches the intestine, where the PPI is released. Individually prepared enteric coating layered units of the proton pump inhibitor (PPI) may be mixed into the SEDDS melt. Alternatively the PPI's may be filled into a capsule filled with solidified SEDDS, where a layer of protective paraffin may be needed between SEDDS and the prepared PPI pellets. In still an alternative embodiment the prepared PPI pellets may be mixed into a liquid SEDDS formulation.

The combination may thus either be a fix combination, i.e. as a formulation where the NO-releasing NSAID(s) and the acid susceptible proton pump inhibitor are mixed and thereafter filled into a suitable dosage unit. In an alternative embodiment of the invention the acid susceptible proton pump inhibitor may be filled into a capsule with an already solidified SEDDS formulation of one or more NO-releasing NSAID(s)—in this case a layer of protective paraffin or other inert material may be required between the SEDDS formulation and the acid susceptible proton pump inhibitor. In still an alternative embodiment the acid susceptible proton pump inhibitor is mixed into a liquid SEDDS formulation of the NO-releasing NSAID(s).

In an alternative embodiment of the invention, the NO-releasing NSAID(s) and the PPI may be provided in form of a kit, where the NO-releasing NSAID and the PPI are administered sequentially, i.e. one after the other. The order of administration is not crucial, meaning that either of the NO-releasing NSAID or the PPI may be administered before the other. Thus, one embodiment of the invention comprises a combination treatment where one or more NO-releasing NSAIDs are administered to a patient in need of treatment, whereafter a PPI is administered, or vice versa.

Examples of proton pump inhibitors suitable in a combination with a NO-releasing NSAID in accordance with the present invention as stated above, is a compound of the general formula II or a pharmaceutically acceptable alkaline salt thereof, or one of its single enantiomer or an alkaline salt of the single enantiomer.

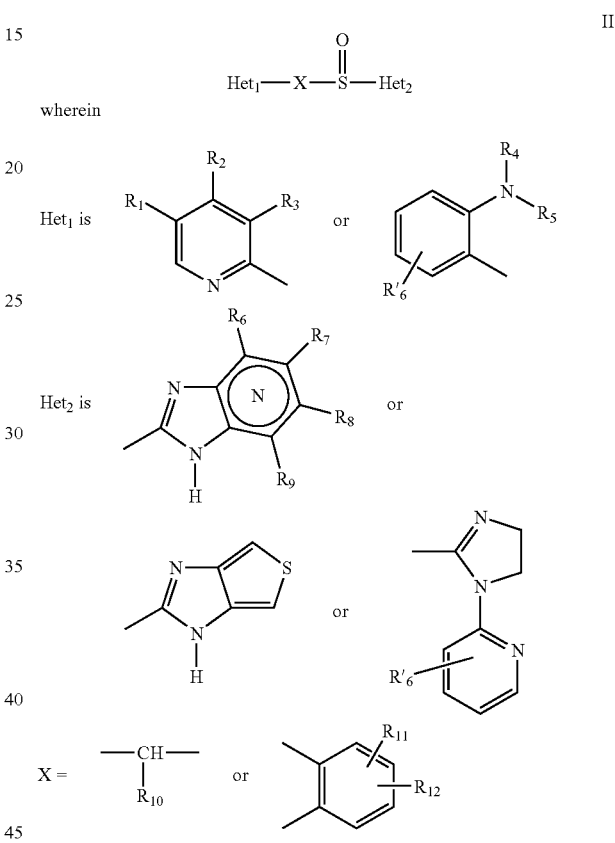

wherein

N in the benzimidazole moiety means that one of the carbon atoms substituted by $R_6$-$R_9$ optionally may be exchanged for a nitrogen atom without any substituents;

$R_1$, $R_2$ and $R_3$ are the same or different and selected from hydrogen, alkyl, alkoxy optionally substituted by fluorine, alkylthio, alkoxyalkoxy, dialkylamino, piperidino, morpholino, halogen, phenyl and phenylalkoxy;

$R_4$ and $R_5$ are the same or different and selected froth hydrogen, alkyl and aralkyl;

$R_6$' is hydrogen, halogen, trifluoromethyl, alkyl and alkoxy, $R_6$-$R_9$ are the same or different and selected from hydrogen, alkyl, alkoxy, halogen, haloalkoxy, alkylcarbonyl, alkoxycarbonyl, oxazolyl, trifluoroalkyl, or adjacent groups $R_6$-$R_9$ form ring structures which may be further substituted;

$R_{10}$ is hydrogen or forms an alkylene chain together with $R_3$ and $R_{11}$ and $R_{12}$ are the same or different and selected from hydrogen, halogen or alkyl; alkyl groups, alkoxy groups and moieties thereof, they may be branched or straight $C_1$-$C_9$-chains or comprise cyclic alkyl groups, such as cycloalkyl-alkyl.

Examples of specific proton pump inhibitors suitable in accordance with the present invention are

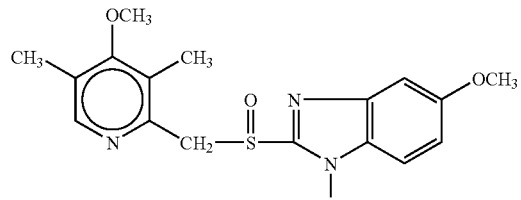
Omeprazole

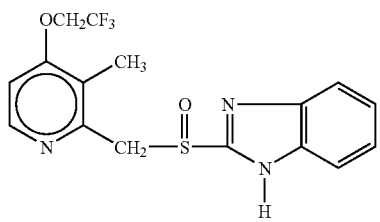
Lansoprazole

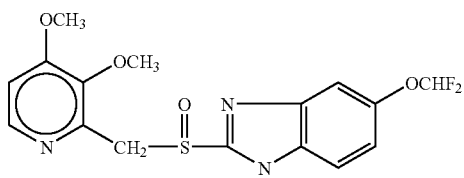
Pantoprazole

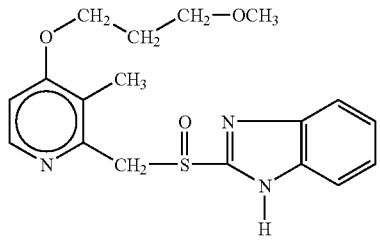
Pariprazole

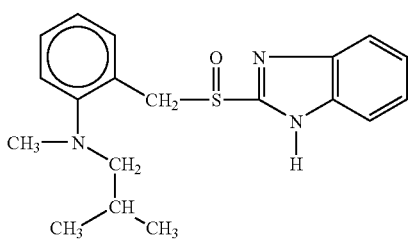
Leminoprazole

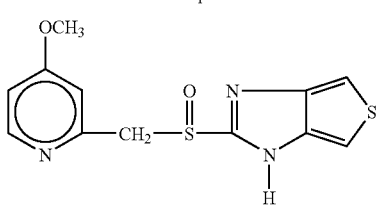

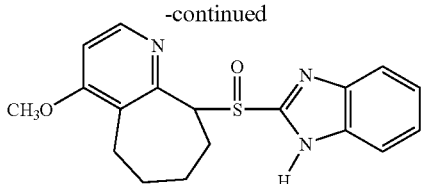

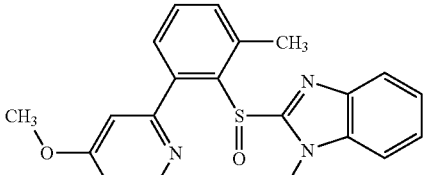

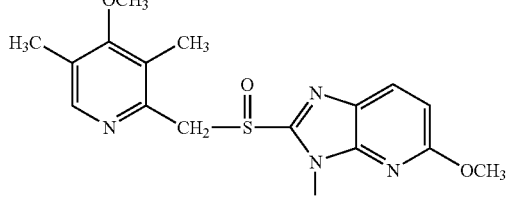

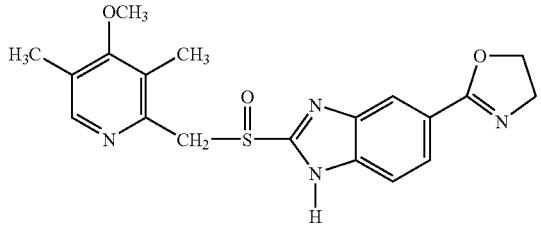

The acid susceptible proton pump inhibitors used in the dosage forms of the invention may be used in their neutral form or in the form of an alkaline salt, such as for instance the $Mg^{2+}$, $Ca^{2+}$, $Na^+$, $K^+$ or $Li^+$ salts, preferably the $Mg^{2+}$ salts. Further where applicable, the compounds listed above may be used in racemic form or in the form of the substantially pure enantiomer thereof, or alkaline salts of the single enantiomers.

Suitable proton pump inhibitors are for example disclosed in EP-A1-0005129, EP-A1-174 726, EP-A1-166 287, GB 2 163 747 and WO 90/06925, and further especially suitable compounds are described in WO 95/01977 and WO94/27988.

The proton pump inhibitors used in a combination in accordance with the present invention, are preferably provided as enteric coating layered pellets comprising the acid susceptible proton pump inhibitor. For the composition of the enteric coating layered pellets and its preparation, reference is made to WO 96/01623, which is hereby incorporated by reference.

Suitable combinations in accordance with the present invention are for instance a NO-releasing NSAID of the formula Ia and omeprazole or an alkaline salt of omeprazole, (S)-omeprazole or an alkaline salt of (S)-omeprazole; or a NO-releasing NSAID of the formula Ii and omeprazole or an alkaline salt of omeprazole, (S)-omeprazole or an alkaline salt of (S)-omeprazole.

The pharmaceutical composition of the invention is filled into unit dosage forms suitable for oral administration, such as capsules, drinking ampoules and dose cushions, or may be formulated as other suitable oral unit dosage forms such as chewable soft pills and chewy-base lozenges.

In a preferred embodiment of the invention, the pharmaceutical composition is filled into hard gelatine capsules, but capsules from alternative materials such as methyl cellulose-based shells, and soft gelatine capsules may also be used.

In an alternative embodiment of the invention, the pharmaceutical composition may be dissolved in e.g. a glass of water, thus allowing the pre-concentrate to form an emulsion which may be administered as such. The compositions intended for dissolution prior to administration may be filled e.g. into soft gelatine capsules, plastic or aluminium cushions, or plastic or glass ampoules. This feature is particularly advantageous for high dose compositions, which would require a large capsule, for patients who have difficulty in swallowing capsules, and for paediatric patients.

In a preferred embodiment the pharmaceutical composition of the present invention is filled into capsules. Preferred capsules are gelatine capsules, which may be soft or hard. The hard gelatine capsule consists of two pieces, a cap and a body, one fitting inside the other. The hard gelatine capsules are produced empty and filled in a separate operation step. The soft gelatine capsule is a capsule, which is manufactured and filled, in one single operation.

As mentioned above, the emulsion pre-concentrate transforms into an oil-in-water emulsion upon contact with the gastrointestinal fluids, whereby the active drug is released. Thus, the composition will form an in situ oil-in-water emulsion in the gastrointestinal tract (GI tract).

The pharmaceutical composition of the present invention is particularly useful in the treatment of pain and inflammation. The wording "pain" is intended to include, but not limited to, nociceptive and neuropathic pain or combinations thereof; acute, intermittent and chronic pain; cancer pain; migraine and headaches of similar origin. The wording "inflammation" is intended to include, but not limited to, rheumatoid arthritis; ostheoarthritis; and juvenile arthritis.

Methods of Preparation

The pharmaceutical composition of the present invention may be prepared mainly by the following alternative methods:

I. Mixing a) The oily or semi-solid NO-releasing NSAID is put in a vessel, phospholipid, and optionally, a solid, semi-solid surfactant or solid/oily fat is added. The mixture is gently heated, making the formulation fluid, mixed thoroughly until homogenous (visual inspection) and the pre-concentrate is filled into capsules suitable for oral administration.

b) Alternatively, the oily NO-releasing NSAID is put in a vessel and phospholipid, and optionally; a fluid surfactant is added. The mixture is mixed thoroughly until homogenous (visual inspection) and the pre-concentrate is filled into capsules suitable for oral administration.

c) In a further alternative method, the oily NO-releasing NSAID is put in a vessel together with phospholipid, and finely grinded (particle size <177 um) solid surfactant is added. The liquid mixture is mixed thoroughly until homogenous (visual inspection) and the pre-concentrate is filled into capsules suitable for oral administration.

d) In still an alternative method the phospholipid and optionally, a semi-solid/solid surfactant(s) are put in a vessel, and one or more alcohols are added. The mixture is heated to the temperature corresponding to the melting point of the excipients, making the formulation fluid, mixed thoroughly until homogenous (visual inspection). The NO-releasing NSAID is added, and the mixture is mixed thoroughly until homogenous (visual inspection). The pre-concentrate is filled into capsules suitable for oral administration.

e) In yet a further alternative method the phospholipid optionally in mixture with a liquid surfactant(s) is put in a vessel, and one or more alcohols are added. The mixture is blended thoroughly until homogenous (visual inspection). The NO-releasing NSAID is added, and the mixture is mixed thoroughly until homogenous (visual inspection). The pre-concentrate is filled into capsules suitable for oral administration.

In order to fill a two-piece capsule or a soft gel capsule with a liquid, the formulation must be within a certain viscosity range, as determined by the manufacturer, at the filling temperature suitable for the process. For a two-piece capsule the maximum filling temperature is roughly 70° C. The viscosity of the formulation should normally be in the range 50-1000 cPoise (=0.05-1 Pas) at the temperature chosen for the filling process. For the filling of the formulation into soft gel capsules, process temperature is not allowed to exceed 30-40° C. (the exact temperature depending on the manufacturer). The formulation must be liquid and have a viscosity that allows it to be pumpable at the filling temperature. In order to make the formulation liquid with an acceptable viscosity, several additives may be used, for example Cremophor EL® or fractionated coconut oil.

II. Filling

For the filling procedure it is required that the composition is in liquid form at the temperature of filling. Semisolid thermosoftening compositions are therefore filled above the liquefying temperature. Soft gelatine capsules are manufactured and filled in one operation, and may be filled at temperatures of up to 40° C., whereas hard gelatine capsules may be filled at temperatures of up to 70° C. Hard gelatine capsules filled with compositions that remain liquid at storage temperature require sealing, e.g. by gelatine banding, to prevent leakage. The process of liquid filling of hard gelatine capsules and product requirements are e.g. described in W. J. Bowtle, *Pharmaceutical Technology* Europe, October 1998; V. M. Young, *Pharmaceutical Manufacturing and Packaging Sourcer*, March 1999; and E. T. Coole, *Pharmaceutical Technology International*, September/October 1989. Using two piece capsules permits filling of more than one phase into a single capsule, which may be desired for bi- or multiphase drug release (W. J. Bowtle, et al., *Int. J. Pharm.* 141 (1996), pp. 9-16). Several phases of solidifying material can be filled in single steps. The final phase may be liquid if required. The number of phases is only restricted by the capsule size, and volume of the single phases. This special feature may also allow controlled release or separation of different drug substances formulated in the same capsule. Additionally, capsules may be processed further, e.g. by enteric coating.

III. Combination with PPI's

The oily or semi-solid NO-releasing NSAID is put in a vessel, phospholipid and optionally a solid or semi-solid surfactant and optionally a solid/oily fat is added. The mixture is gently heated, making the formulation fluid, mixed thoroughly until homogenous (visual inspection) and prepared enteric coating layered pellets comprising an acid susceptible proton pump inhibitor are added to the mixture. The pre-concentrate with the suspended PPI-pellets is filled into capsules, where it solidifies, suitable for oral administration.

Alternatively the oily or semi-solid NO-releasing NSAID is put in a vessel, solid surfactant and solid/oily fat (optional) is added. The mixture is heated to the temperature corresponding to the melting point of the excipients, making the formulation fluid, mixed thoroughly until homogenous (visual inspection). The pre-concentrate is filled into capsules suitable for oral administration, where it solidifies. A protective layer of paraffin, or any other inert thermo softening base suitable for oral administration, is added and allowed to solidify. On top of the paraffin, the prepared PPI-pellets are added.

In still an alternative method, the oily NO-releasing NSAID is put in a vessel, phospholipid and optionally a fluid surfactant are added. The mixture is mixed thoroughly until homogenous (visual inspection), and the prepared PPI-pellets are added to the mixture. The pre-concentrate with suspended PPI-pellets is filled into capsules suitable for oral administration.

IV. Characterisation of the Formulations

In order to characterise formulations, the time required for the formulation to form an oil-in-water emulsion upon contact with simulated gastric fluid, SGF, (without enzymes), is determined, and the formed emulsion is characterised. SGF comprises of 7 milliliters concentrated hydrochloric acid, 2 grams of sodium chloride and distilled water to give the solution a total volume of 1 L. The "emulsion-forming test" is performed in test tubes (beaker) with magnetic stirring. The test tube, containing a small magnet, is filled with 12.5 ml SGF without enzymes, corresponding to one tenth of the average volume of gastric fluid in humans, and formulation corresponding to one tenth of the dose of active compound is added. If the formulation being characterised is a combination with a PPI, the PPI-pellets are checked in order that they are unaffected by the SGF, which is made by visual inspection. If the enteric coating of the PPI-pellets is affected, the PPI may be affected negatively in pH=1.2, and this can be observed as a marked change in colour.

The time for emulsion formation will vary from 30 seconds and up to 15 minutes, depending on the composition of the formulation. If one or more short-chain alcohols are added, the time for emulsion formation will vary between 2-3 seconds and 3-4 minutes.

DETAILED DESCRIPTION OF THE INVENTION

The invention will now be described in more detail by the following examples, which are not to be construed as limiting the invention.

In the following examples, the active compound used in the formulation was a compound of the formula (Ia) above.

Formulation were prepared by dissolving the phospholipid in a co-solvent such as propylene glycol, glycerol or ethanol, and then adding the active compound to the mixture:

| Formulation 1 | |
|---|---|
| Lipoid S100 | 0.30 g |
| Propylene glycol | 0.90 g |
| Compound of formula Ia | 4.00 g |
| Formulation 2 | |
| Lipoid S100 | 0.30 g |
| Glycerol | 0.90 g |
| Compound of formula Ia | 4.00 g |
| Formulation 3 | |
| Lipoid S100 | 0.24 g |
| Etanol | 0.96 g |
| Compound of formula Ia | 4.00 g |
| Formulation 4 | |
| Lipoid E80 | 0.30 g |
| Propylene glycol | 0.90 g |
| Compound of formula Ia | 4.00 g |

-continued

| Formulation 5 | |
|---|---|
| Lipoid E80 | 0.30 g |
| Glycerol | 0.90 g |
| Compound of formula Ia | 4.00 g |
| Formulation 6 | |
| Lipoid E80 | 0.30 g |
| Ethanol | 0.90 g |
| Compound of formula Ia | 4.00 g |
| Formulation 7 | |
| Lipoid S75 | 0.30 g |
| Propylene glycol | 0.90 g |
| Compound of formula Ia | 4.00 g |
| Formulation 8 | |
| Lipoid S75 | 0.30 g |
| Glycerol | 0.90 g |
| Compound of formula Ia | 4.00 g |
| Formulation 9 | |
| Lipoid S75 | 0.30 g |
| Ethanol | 0.90 g |
| Compound of formula Ia | 4.00 g |

The emulsifying formulations were tested in a self-emulsifying test (described on page 24)

The dissolution of the drug was measured according to the paddle method in US Pharmacopoeia (US Pharmacopoeia 24/NF 19, 200).

| Formulation | Time to emulsion formation | Amount (%) dissolved drug after 200 minutes |
|---|---|---|
| 1 | 1-2 minutes | 6-8 |
| 2 | 1-2 minutes | 6-7 |
| 3 | 1-2 minutes | 8-10 |
| 4 | 1-2 minutes | 8-10 |
| 5 | 1-2 minutes | 8-10 |
| 6 | 1-2 minutes | 8-10 |
| 7 | 1-2 minutes | 10-13 |
| 8 | 1-2 minutes | 8-10 |
| 9 | 1-2 minutes | 10-13 |

The bioavailability of the formulations according to the present invention may be tested by oral administration in fastened minipigs.

The invention claimed is:

1. An emulsion pre-concentrate in the form of a liquid consisting essentially of:
   (i) one or more NO-releasing NSAID(s);
   (ii) a phospholipid; and
   (iii) one or more short-chain alcohols,
   and
   wherein the emulsion pre-concentrate forms an in-situ oil-in-water emulsion upon contact with aqueous media.

2. The emulsion pre-concentrate according to claim 1, wherein the NO-releasing NSAID is a compound of the formula I,

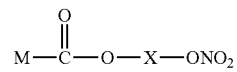

I wherein:

X is a spacer; and

M is a structure selected from the group consisting of:

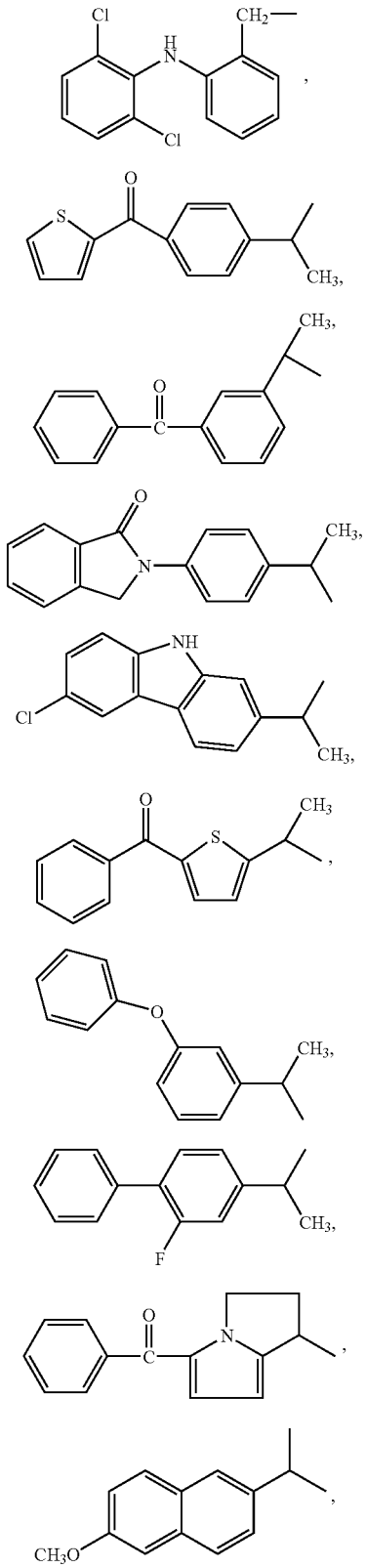

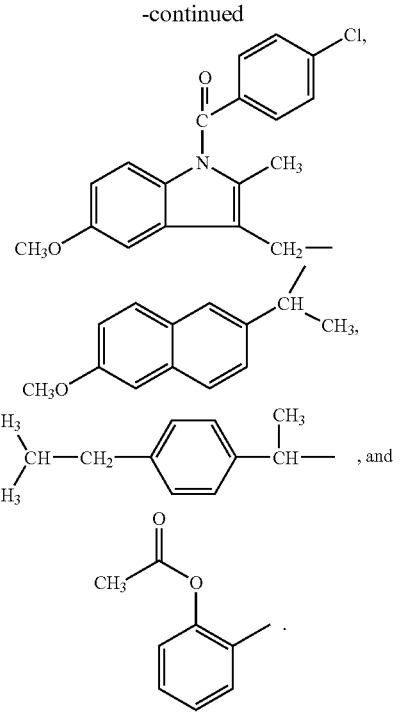

3. The emulsion pre-concentrate according to claim 2, wherein the spacer X of the NO-releasing NSAID is selected from the group consisting of:

a linear, branched or cyclic alkylene group;

—(CH$_2$)—$_n$ wherein n is an integer from 2 to 10;

—(CH$_2$)$_m$—O—(CH$_2$)$_p$— wherein m and p are integers from 2 to 10; and

—(CH$_2$)$_p$—C—6H$_4$—CH$_2$— wherein p is an integer from 2 to 10.

4. The emulsion pre-concentrate according to claim 1, wherein the NO-releasing NSAID is a compound selected from the group consisting of:

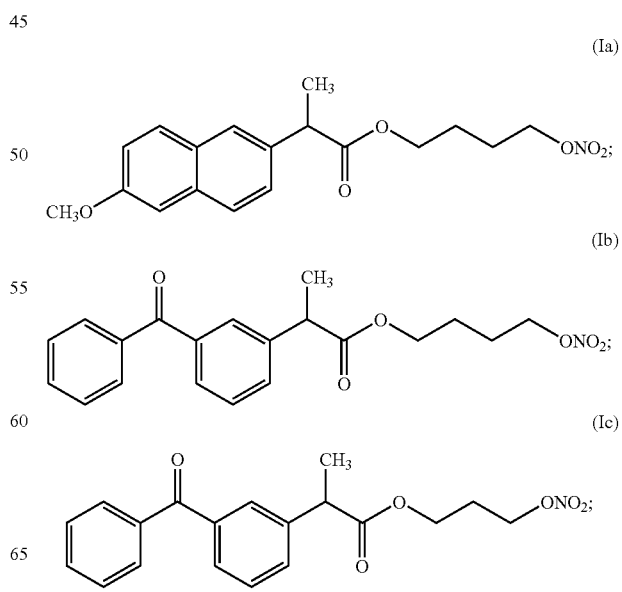

5. The emulsion pre-concentrate according to claim 1, wherein the amount of the NO-releasing NSAID is from 50-1500 mg per unit dose.

6. The emulsion pre-concentrate according to claim 5, wherein the amount of the NO-releasing NSAID is from 125-500 mg per unit dose.

7. The emulsion pre-concentrate according to claim 1, wherein the phospholipid is lecithin.

8. The emulsion pre-concentrate according to claim 7, wherein the lecithin is egg lecithin, soya lecithin, or a mixture thereof.

9. The emulsion pre-concentrate according to claim 1, wherein the short-chain alcohol is ethanol, propylene glycol, or glycerol.

10. A unit dosage form comprising the emulsion pre-concentrate of claim 1 and excipients for formulating the unit dosage form.

11. The unit dosage form according to claim 10, wherein the dosage form is a capsule.

12. The unit dosage form according to claim 11, wherein the capsule is a hard gelatine capsule.

13. The unit dosage form according to claim 11, wherein the capsule is a soft gelatine capsule.

* * * * *